United States Patent [19]

Pietsch et al.

[11] Patent Number: 4,902,728

[45] Date of Patent: Feb. 20, 1990

[54] SURGICAL MATERIAL

[75] Inventors: Hanns Pietsch, Hamburg; Karl G. Doppler, Lübeck; Barbara Krug, Hamburg; Wolfgang Meyer-Ingold, Hamburg; Ingrid Wesselkamp, Hamburg; Volker Hohmann, Norderstedt; Ernst-Joachim Henssge; Andre Ljutow, both of Lübeck, all of Fed. Rep. of Germany

[73] Assignee: Beiersdorf Aktiengesellschaft, Hamburg, Fed. Rep. of Germany

[21] Appl. No.: 268,420

[22] Filed: Nov. 8, 1988

[30] Foreign Application Priority Data

Nov. 12, 1987 [DE] Fed. Rep. of Germany ....... 3738422

[51] Int. Cl.[4] .............................................. A01F 2/28
[52] U.S. Cl. .................................... 523/115; 523/116; 524/173
[58] Field of Search ................. 523/115, 116; 524/173

[56] References Cited

U.S. PATENT DOCUMENTS 4,563,184 1/1986 Korol .................................. 604/368
4,588,583 5/1986 Pietsch et al. ........................ 424/81

OTHER PUBLICATIONS

Barilyak, I. R.; Kalinous Kaya, L. P. Chem. Abstracts, "Study of the Embryotoxic Activity of Dimexide" DMSO, vol. 90, 79.

Primary Examiner—Joseph L. Schofer
Assistant Examiner—John J. Guarriello
Attorney, Agent, or Firm—Sprung, Horn, Kramer & Woods

[57] ABSTRACT

In a surgical composition comprising a liquid monomeric and powdered polymeric acrylate or methacrylate, a catalyst and an accelerator, the composition upon mixing of the liquid and powdered constituents passing through a plastic state to a solid state, the improvement which comprises including in the composition about 1 to 15% by weight of dimethyl sulfoxide. The product exhibits reduced cytotoxicity.

7 Claims, No Drawings

SURGICAL MATERIAL

BACKGROUND OF THE INVENTION

The invention relates to a surgical material based on liquid monomeric and powdered polymeric acrylates and/or methacrylates that changes into solid state by way of a plastic state due to the addition of catalysts, accelerators, and, optionally, conventional additives once the liquid and powdered constituents have been mixed together. The resulting pastes are especially appropriate for use as "bone cements" in the implantation of artificial hip and knee joints, and the like, in bone.

Bone cements based on methyl methacrylate and polymethyl methacrylate have been employed in bone surgery for many years. They consist of a liquid constituent and of a solid constituent that are stored separately and mixed together for use. The mixture is pasty or creamy and is employed in that state, curing subsequent to application in the body. The solid constituent usually consists of powdered polymethyl methacrylate, a polymerization initiator, and optionally an X-ray contrast agent such as barium sulphate or zirconium dioxide. The powder can also include such antibiotics as gentamicin, such short reinforcing fibers as carbon fibers, and such bone-growth promoters as calcium phosphate. The liquid constituent consists of monomeric methyl methacrylate, an accelerator, and optionally a dye. The two constituents are mixed in a ratio of approximately 2:1 just before processing, are ready to use in approximately 4 to 6 minutes, and cure in 6 to 15 minutes.

The advantages of bone cements of this type are their good compatibility with the tissue, their rapid curing rate, and the powerful strength of the hardened cement. In contrast to these advantages, however, are such drawbacks as the comparatively high temperatures that occur during polymerization and can lead to damage to the surrounding tissue and hence to loosening of the bond.

Another drawback of the methyl-methacrylate based cements employed in joint operations up to now is their release of residual monomers. Monomeric methyl methacrylate gets into the bloodstream and can lead to fatty embolisms that entail cardiocirculatory complications severe enough to cause cardiac arrest.

These drawbacks are eliminated by a bone cement described in German patent No. 2 552 070, which contains a liquid constituent in the form of an emulsion of methyl methacrylate, water, an emulsifier, and an accelerator. Bone cements prepared in accordance with this method have a lower maximal curing temperature and a lower content of residual monomer, and wet the irregularities in the surface of the bone better.

In addition to these advantages, however, emulsion-type cements have drawbacks, especially in relation to convenience. The emulsions have viscosities of 200 to 800 MPa·sec and have to be vigorously shaken before they can be poured out of the ampoule. Shaking, however, is inconvenient and time-consuming while an operation is going on, and extreme care must be taken to ensure that the ampoule is completely emptied and to prevent spattering when the emulsion is knocked out. Furthermore, aqueous emulsions are sensitive to freezing when stored.

German patent application No. 3 245 956.4 describes a bone cement with a liquid constituent that contains aliphatic esters of saturated mono-, di-, or tri-carboxylic acids with 1 to 6 carbon atoms and optionally either 1 or 2 hydroxy groups partly or completely esterified with 1-, 2-, or 3-valence alcohols with 1 to 4 carbon atoms, or liquid esters, specifically polyethylene glycol or 1,2- or 1,3-polypropylene glycol, each with 2 to 30 glycol units.

It has, however, become evident that, although the aforesaid liquids do have the advantages described in the application and are not toxic in general, they possess a certain cytotoxicity.

OBJECT OF THE INVENTION

The object of the present invention is accordingly to provide a bone cement that has the advantages of the substance described in application No. 3 245 956 along with lower cytotoxicity.

This object is attained in accordance with the invention in a surgical paste of the type initially described that contains 1 to 15% by weight of dimethyl sulfoxide in terms of its total weight.

It has, surprisingly, been discovered that surgical pastes of this type cure at lower temperatures, contain lower levels of residual monomers, wet the surface of the bone very satisfactorily, provide better adhesion to the alloys that the implants are made of, and exhibit a lower cytotoxicity.

Dimethyl sulfoxide is known as a good solvent. It mixes completely with methyl methacrylate, N,N-dimethyl-p-toluidine, which is a conventional polymerization accelerator, and water, and is an excellent solvent for polymethyl methacrylate. It is also cytocompatible, as research has demonstrated. In this respect it is superior to the ethers and esters cited in German application No. 3 245 956. Only glycerol is more cytocompatible, but does not possess the solubilization properties of dimethyl sulfoxide.

The satisfactory intermiscibility of all its constituents results in outstanding flow properties of the part of the viscous bone cement in accordance with the invention, which can accordingly be handled and applied in many different ways, by hand or with a syringe for example. It is even possible to employ a cement gun.

The dimethyl sulfoxide in one preferred embodiment of the invention is mixed into the liquid monomers.

The liquid constituent in a preferred variant of this embodiment contains 5 to 30% and preferably 15 to 20% by weight of dimethyl sulfoxide.

The liquid mixtures of methyl methacrylate, dimethyl sulfoxide, accelerator, and optionally 0 to 5% of a surfactant are mixed with the mixture of powder before being used. The mixture of powder usually consists of a polymethyl-methacrylate bead polymer, a polymerization initiator and optionally an X-ray contrast agent. The ratio of powder to liquid is 1 to 4 and preferably 1.5 to 3. The dimethyl sulfoxide in the liquid constituent in accordance with the invention amounts to 1 to 15% of the paste created by mixing the liquid and powdered constituents.

It has been demonstrated that mixtures of this type will satisfactorily wet the uneven surface of the bone. This property, along with that of filling even the smallest cracks, can, however, be improved even more by adding a certain percentage of surface-active (interface-active) substances. Preferable for this purpose are such non-ionic and cation-active compounds as the fatty-acid esters of sorbitan of ethoxylated sorbitan and of sorbitol, ethoxylated fatty acids, ethoxylated aliphatic alcohols, partial fatty-acid esters of glycerol, ethoxylated partial fatty-acid esters of glycerol, alkyldimethylbenzyl ammonium chloride, alkylammonium benzoate, alkylammonium lactate, cetylpyridinium chloride, dodecyl di(β-oxyethyl)benzylammonium chloride, or soybean trimethyl ammonium chloride, all of which can be employed alone or in the mixture.

The liquid constituent can also contain low levels of such other auxiliaries as dyes for example.

The powdered solid constituent of the surgical material consists in a way that is in itself known primarily of very fine-grained polymethyl methacrylate (with a mean grain diameter of up to 200 μm), optionally of low levels of modifying other polyacrylate derivatives or copolymers thereof, such as for example methyl methacrylate and ethylacrylate, methyl methacrylate and butyl methacrylate, methyl methacrylate and methyl acrylate, or methyl methacrylate and butyl acrylate, of the polymerization initiator, which is usually approximately 1 to 2% dibenzoyl peroxide, and of an X-ray contrast agent such as for example zirconium dioxide, cerium dioxide, thorium dioxide, barium sulfate, or calcium sulfate.

These constituents can also contain other additives, such as antibiotics, biodegradable substances such as tricalcium phosphate and collagen, bioactive vitreous ceramics or reinforcing fibers of carbon for example, polyesters, polyvinyl alcohol, or polyamide.

In using the surgical material, often in the implantation of an artificial hip for example, the requisite amounts of the separately stored sterile constituents are blended into a uniform paste and must then be used rapidly because the polymerization reaction commences immediately with self-heating, and the paste will cure rapidly.

The following examples have been carried out to demonstrate the properties of the surgical mixtures in accordance with the invention. The properties were measured in accordance with DIN-ISO Standard 5833 for bone cements. The levels of residual monomers were determined by gas chromatography with headspace analysis. The cytocompatibility (cytotoxicity) of dimethyl sulfoxide was determined from its action on mouse connective-tissue cells (3T3) and yielded an $ID_{50}$ of approximately 29.9 mg/ml.

EXAMPLES 1-6

| Example | Methylmeth-acrylate % by weight | Dimethyl sulfoxide % by weight | N,N—dimethyl p-toluidine % by weight |
|---|---|---|---|
| 1 | 94 | 5 | 1 |
| 2 | 89 | 10 | 1 |
| 3 | 84 | 15 | 1 |
| 4 | 79.2 | 20 | 0.8 |
| 5 | 74.2 | 25 | 0.8 |
| 6 | 69.2 | 30 | 0.8 |

These mixtures are clear and homogeneous liquids at room temperature that will flow out of an ampoule made of Hydrolytic Class 1 glass in a few seconds without being shaken.

Always 18 g of these liquid mixtures have been mixed with 42 g of a powdered mixture consisting of 88.6% by weight polymethyl metacrylate, 10% by weight zirconium dioxide powder and 1.4% by weight dibenzoyl peroxide.

The following DIN-ISO 5833 levels were measured while the pastes were curing:

| Example | 1 | 2 | 3 | 4 | 5 | 6 |
|---|---|---|---|---|---|---|
| Curing time, min. | 12.5 | 11.5 | 11.5 | 11.0 | 11.0 | 10.5 |
| Max. Curing temp., °C. | 51.3 | 51.0 | 50.0 | 49.0 | 48.3 | 48.5 |
| Intrusion, mm | 7 | 7.5 | 6 | 6.5 | 6 | 7 |
| Compression strength, MPa | 105.3 | 94.6 | 91.2 | 67.2 | 63.4 | 62.8 |
| Depth of penetration, mm | 0.133 | 0.154 | 0.159 | 0.171 | 0.203 | 0.210 |
| Recovery, % | 81 | 81 | 80 | 76 | 71 | 64 |
| Residual monomer level, % | <1.0 | <1.0 | <1.0 | <1.0 | <1.0 | <1.0 |

It is understood that the specification and examples are illustrative but not limitative of the present invention and that other embodiments within the spirit and scope of the invention will suggest themselves to those skilled in the art.

What is claimed is:

1. In a surgical composition comprising a liquid monomeric and powdered polymeric acrylate and/or methacrylate, a catalyst and an accelerator, the composition upon mixing of the liquid and powdered constituents passing through a plastic state to a solid state, the improvement which comprises including in the composition about 1 to 15% by weight of dimethyl sulfoxide.

2. A surgical composition according to claim 1, wherein the dimethyl sulfoxide is first incorporated into the liquid constituent.

3. A surgical composition according to claim 2, wherein dimethylsulfoxide is present in from about 5 to 30% by weight of the liquid constituent.

4. A surgical composition according to claim 2, wherein dimethylsulfoxide is present in from about 15 to 20% by weight of the liquid constituent.

5. A surgical composition according to claim 1, wherein the weight ratio of powdered to liquid constituent is about 1 to 4.

6. A surgical composition according to claim 1, wherein the weight ratio of powdered to liquid constituent is about 1.5 to 3.

7. In the cementing of bone wherein a cement is applied to bone components or substitutes and the cement is permitted to harden, the improvement which comprises employing as the cement a composition according to claim 1.

* * * * *